United States Patent [19]

Cherry et al.

[11] 3,968,054

[45] July 6, 1976

[54] CATALYST FOR THE OXIDATION OF BUTANE TO MALEIC ANHYDRIDE

[75] Inventors: Wesley E. Cherry, Prospect Park; Alan F. Dickason, Chester, both of Pa.; John A. Hedge, Wilmington, Del.

[73] Assignee: Sun Ventures, Inc., St. Davids, Pa.

[22] Filed: Apr. 21, 1975

[21] Appl. No.: 570,289

Related U.S. Application Data

[62] Division of Ser. No. 407,340, Oct. 17, 1973, Pat. No. 3,928,392.

[52] U.S. Cl. ............................... 252/468; 252/467; 252/470
[51] Int. Cl.² ..................... B01J 23/06; B01J 23/28; B01J 23/84
[58] Field of Search ..................... 252/467, 468, 470

[56] References Cited
UNITED STATES PATENTS
3,907,834  9/1975  Milberger et al. .............. 252/467 X
FOREIGN PATENTS OR APPLICATIONS
2,072,336  9/1971  France .............................. 260/346.8

*Primary Examiner*—W. J. Shine
*Attorney, Agent, or Firm*—J. Edward Hess; Donald R. Johnson; Stanford M. Back

[57] ABSTRACT

A catalyst comprising SB-Ni-Mo has been found to be very selective, stable and long-lasting in the conversion of butane to maleic anhydride. Other metals such as Co, Cu, or Zn may be substituted for Ni with like results. An improved method for preparing this catalyst is also provided herein.

2 Claims, No Drawings

3,968,054

CATALYST FOR THE OXIDATION OF BUTANE TO MALEIC ANHYDRIDE

BACKGROUND OF THE INVENTION

This is a division of application Ser. No. 407,340, filed Oct. 17, 1973, now U.S. Pat. No. 3,928,392.

This invention relates to a novel method for the catalytic vapor phase oxidation of butane with oxygen or air to form maleic anhydride wherein there is employed as the catalyst system an oxide composition containing antimony, molybdenum, and a third metal selected from the group consisting of Ni, Co, Cu, and Zn. This invention also relates to a novel method for preparing this catalyst.

The vapor phase oxidation of butane to maleic anhydride using various combinations of metals, metal oxides and/or metal salts as catalysts is well known in the art as shown, for example, in U.S. Pat. Nos. 2,625,519 and 2,691,660 (e.g., Co/Mo); 3,074,969 (e.g., V-Mo-alkali metal chloride); 3,293,268 (e.g., V/P) and 3,055,842 (e.g., V/Ti/Mo/Al), as well as Belgian Pat. No. 771,795 teaching the use of a four-component vanadium-containing catalyst.

SUMMARY OF THE INVENTION

In accordance with the present invention, it has now been found that an oxide composition containing antimony, molybdenum, and a third metal selected from the group consisting of nickel, cobalt, copper, and zinc, provides an effective catalyst for the vapor phase oxidation of butane to maleic anhydride. This catalyst is characterized in particular by its stable level of selectivity at high conversion.

PREPARATION OF THE CATALYST

The catalysts of this invention may conveniently be prepared in a manner similar to the teachings of Canadian Pat. No. 796,787 or U.S. Pat. Nos. 3,595,910 and 3,595,911. Thus, for example, in accordance with these methods, an Sb/Ni/Mo catalyst may be prepared as follows: antimony pentachloride is added to a solution of nickel chloride hexahydrate in water, and the pH of the mixture adjusted to 6.5 with ammonia. The resulting precipitate, after washing, is then mixed with a solution of ammonium molybdate, the mixture dried, the dried cake ground up and calcined in oxygen or air at temperatures of from about 600° – 900°C for several hours, principally at about 700°C.

The resulting catalyst is characterized in being roughly mottled yellow-green in color, and is further characterized in providing selectivities for the desired maleic anhydride in the range of about 25 to 30 percent. Inasmuch as the color characteristics of this catalyst are subject to change, this quality cannot be considered to be a fully established one.

Alternatively, the Sb/Ni/Mo catalyst may be prepared by a somewhat different method which, compared with the above method, advantageously permits substantial control of the quantity of the third metal which is incorporated in the Sb/Mo composition. The first method permits little, if any, latitude in this respect. The catalyst prepared by this alternative method also provides higher selectivities over a longer period of time. When nickel, for example, is employed, the resulting Sb/Ni/Mo catalyst is characterized by providing selectivities of about 25–35 percent. The catalyst is further characterized by a uniform greenish-brown color, but again it will be understood that this color characteristic is not necessarily a fixed one. However, although the applicants do not wish to be bound by any particular theories, it is believed that the yellowish color of the first catalyst represents a partially activated form which provides lower selectivities than does the greenish-brown form. The second catalyst, which is more greenish in color, is therefore, believed to represent a catalyst which is more uniform in composition and properties with respect to selectivity in converting butane to maleic anhydride. Again, while not wishing to be bound by any particular theory, it is believed that the properties of the more uniform catalyst are a result of the temperatures at which it is calcined, i.e., at temperatures of over 750°C and preferably at temperatures of at least 800°C, as described below, and in Example 14.

This alternative form of catalyst may be prepared using, for example, nickel as the third metal, by first dissolving a water-soluble antimony salt such as $SbCl_5$ in water in amount of preferably about 20–25% by weight, preferably at temperatures below 35°C, warming the solution to room temperature, adjusting the pH of the resulting solution with a suitable alkaline reagent such as $NH_4OH$ to about pH 6.5, thereby precipitating said salt, and filtering, washing and drying the resulting precipitate to a moist cake. To this material is then added an aqueous solution of a water-soluble molybdenum salt and nickel salt such as ammonium molybdate and nickel nitrate in amounts of about 5–15% and about 15–25% by weight, respectively. The resulting composition, after evaporation, is dried at about 110° to 130°C for about 15 to 20 hours, crushed to small particle size and calcined at a temperature of from about 750°C to 850°C, and preferably about 800°C for about at least 2 hours, preferably about 3 to 6 hours. It will be understood that in a like manner other Sb/Mo catalyst, where the nickel is substituted by cobalt, or the like, may be prepared by employing salts such as cobalt nitrate, copper chloride, or zinc chloride, as shown, e.g., in U.S. Pat. Nos. 3,595,910 or 3,595,911 (supra).

Analysis of these catalysts reveal that the percentage range of antimony present is about 40 to 90 atomic percent based on the total metals present, and preferably is about 72 to 81 atomic percent. The corresponding atomic percent of nickel and molybdenum is desirably in the range of 5 to 40 percent for nickel, preferably about 8 to 18 percent, and 1 to 20 percent for the molybdenum, preferably 6 to 15 percent, respectively, based on the total metals of the composition. When other metals are substituted for nickel the same general ratios still prevail.

Surprisingly, it has been found that these catalysts are most effective when they are not supported on any inert carrier. That is to say, the presence of a support substantially reduces, or on occasion, nullifies the activity of the catalyst, and it should, therefore, desirably be used alone.

As aforestated, the Sb/Ni/Mo catalysts of this invention may be modified by substituting for the nickel component a metal selected from the group consisting of cobalt, copper, or zinc. This may readily be achieved by simply employing the salts enumerated above, or like soluble salts in place of the nickel chloride compound. Otherwise, the process for preparing the catalyst remains as described above.

OXIDATION OF BUTANE TO MALEIC ANHYDRIDE

The vapor phase oxidation of butane to maleic anhydride, using the aforedescribed catalysts, may conveniently be carried out by passing the butane, together with oxygen and/or air over a bed of said catalyst at temperatures of from about 350° to 650°C, and preferably about 400° to 500°C, at contact times of from about 0.001 sec. to 10 sec., and preferably about 0.1 to 2 sec., and at pressures ranging from atmospheric pressure to about 100 lbs./in.2, where the catalyst bed may be either a fixed bed, a fluidized bed, or a moving bed. The concentration of oxygen in the feed stream may vary within moderately wide limits but should desirably be from about 1 to 20 percent by volume of the total feed stream, and preferably about 15 to 20 percent, while the volume of butane contained in the feed should desirably be from about 0.1 to 10 percent and preferably 1 to 5 percent. It will be understood that the oxygen may be diluted with inert gases, or supplied as air.

The maleic anhydride may be recovered from the reaction product by any conventional method, for example, by passing the effluent through water, then stripping of the water. The catalyst may, when necessary, be readily regenerated by treating it with air or oxygen at temperatures up to 700°C.

This invention will now be illustrated by the following examples.

CATALYST PREPARATIONS

Example 1 — Antimony: Nickel: Molybdenum Catalyst

Antimony pentachloride ($SbCl_5$, 149.5 g.) was added slowly to a stirred solution of nickel chloride hexahydrate ($NiCl_2 6H_2O$, 118.9 g) in 500 milliliters of distilled water. (The temperature increased from 28° to 42°C). The pH of the mixture was adjusted to 6.5 with concentrated aqueous ammonia using an ice bath to keep the temperature below 60°C. The mixture was then stirred for 45 minutes, filtered, the filter cake washed three times by resuspension in 500 milliliter portions of distilled water and filtered again.

The moist filter cake was then mixed with ammonium molybdate [$(NH_4)_6Mo_7O_{24}.4H_2O$, 11.1 g.] in 100 milliliters of distilled water, evaporated to a thick paste on a steam bath, and dried at 110°–120°C for 16 hours. The dried cake was broken to pass a 4 mesh screen and calcined from 25° to 700°C over 8 hours, then held at 700°–725°C for 16 hours.

Example 2 — Antimony: Nickel: Molybdenum Catalyst

Antimony pentachloride ($SbCl_5$, 25 g) was added slowly to distilled water (250 mls.) with stirring. The temperature of the suspension was maintained below 35°C with an ice bath. The suspension was allowed to warm to room temperature, then the pH was adjusted to 6.5 with concentrated aqueous ammonia (about 85 ml) while stirring for 45 minutes. The precipitate was filtered, washed three times with 250 milliliters of distilled water for 15 minutes and filtered again.

Ammonium molybdate [$(NH_4)_6Mo_7O_{24}.4H_2O$, 2.2 g] was dissolved in distilled water (40 ml.) at room temperature. Nickel nitrate hexahydrate [$Ni(NO_3)_2.6H_2O$, 2.8 g] was dissolved in distilled water (10 ml.) at room temperature and then combined with the ammonium molybdate solution.

The combined solution was then added to the moist filter cake and stirred. The mixture was then evaporated to a thick paste while stirring on a steam bath. The paste was dried at 110° to 120°C for 16 hours. The dried cake was crushed to pass a 4-mesh screen and the resulting particles calcined at 800°C for 3 hours.

This procedure was used to prepare catalysts with varying ratios of the three components by changing the concentration of the ammonium molybdate and the nickel nitrate solution.

Example 3 — Antimony: Cobalt: Molybdenum Catalyst

Antimony pentachloride ($SbCl_5$, 149.5 g) was added slowly to a stirred solution of cobalt chloride hexahydrate ($CoCl_2.6H_2O$, 42.5 g.) in 500 milliliters of distilled water. The pH of the mixture was adjusted to 7.0 with concentrated aqueous ammonia using an ice bath to keep the temperature below 60°C. The mixture was stirred for 45 minutes, filtered and the filter cake washed three times by resuspension in 500 milliliter portions of distilled water. The filter cake was dried for 16 hours at 110° to 120°C and crushed to pass a 100-mesh screen.

The 100 mesh powder was then mixed with ammonium molybdate [$(NH_4)_6Mo_7O_{24}.4H_2O$, 11.1 g] in 100 milliliters of distilled water and evaporated to a thick paste on a steam bath. The catalyst was dried at 110° to 120°C for 16 hours crushed to pass a 4-mesh screen, and calcined from 25° to 700°C for 8 hours, then held at 700°–725°C for 16 hours.

Example 4 — Antimony: Copper: Molybdenum Catalyst

Antimony pentachloride ($SbCl_5$, 149.5 g) was added slowly to a stirred solution of copper chloride ($CuCl_2$, 16.8 g) in 500 milliliters of distilled water. (The temperature increased from 28°C to 42°C). The pH of the mixture was adjusted to 6.5 with concentrated aqueous ammonia using an ice bath to keep the temperature below 60°C. The mixture was stirred for 45 minutes, filtered, the filter cake washed three times by resuspension in 500 milliliter portions of distilled water and filtered again.

The moist filter cake was then mixed with ammonium molybdate [$(NH_4)_6Mo_7O_{24}.4H_2O$, 11.1 g] in 100 milliliters of distilled water, evaporated to a thick paste on a steam bath and dried at 110° to 120°C for 16 hours. The dried cake was broken to pass a 4 mesh screen and calcined from 25° to 700°C over 8 hours, then held at 700°–725°C for 16 hours.

Example 5 — Antimony: Zinc: Molybdenum Catalyst

Zinc powder (16.4 g) was dissolved in concentrated hydrochloric acid (177 g) keeping the temperature at about 30°C with an ice bath. Antimony pentachloride ($SbCl_5$, 128 g) was added slowly to the zinc chloride solution. The pH was adjusted to 7.0 by the slow addition of aqueous ammonia, maintaining the temperature below 60°C in an ice bath. The mixture was stirred for 45 minutes, filtered, the filter cake washed three times by resuspension in 500 milliliter portions of distilled water and filtered again.

The moist filter cake was then mixed with ammonium molybdate [$(NH_4)_6Mo_7O_{24}.4H_2O$, 44.2 g] in 100 milliliters of distilled water, evaporated to a thick paste on a steam bath and dried at 110° to 120°C for 16 hours. The dried cake was broken to pass a 4 mesh screen and calcined from 25° to 700°C over 8 hours, then held at 700°–725°C for 16 hours.

Example 6—Cobalt/Molybdenum Catalyst

Molybdenum trioxide ($MoO_3$, 72g) was slowly added to concentrated aqueous ammonia (140 mls.) then diluted to 500 milliliters with distilled water. The mixture was stirred until all the molybdenum trioxide dissolved and then diluted to 2 liters with distilled water. Boric acid (50g.) was added to buffer the solution and the temperature was increased to 95°C.

Cobalt nitrate [$Co(NO_3)_2 \cdot 6H_2O$, 87.4 g] was dissolved in 200 milliliters of distilled water and heated to 90°C. The hot cobalt nitrate solution was poured into the stirring molybdenum solution forming a blue precipitate. The precipitate was filtered hot and the filter cake air dried for 1 hour with tamping. The filter cake was dried for 16 hours at 110°–120°C, then crushed to pass a 4-mesh sieve. The 4-mesh particles were calcined in a tube with flowing air for 3.5 hours at 350°C.

Example 7 — Nickel Molybdate Catalyst

Molybdenum trioxide ($MoO_3$, 72 g) was slowly added to nickel nitrate hexahydrate [$Ni(NO_3)_2 \cdot 6H_2O$, 145.5 g] then diluted to 300 milliliters with distilled water. The mixture was stirred until all the molybdenum trioxide dissolved and then diluted to 2 liters with distilled water. Boric acid (50 g.) was added to buffer the solution and the temperature was increased to 95°C.

Cobalt nitrate ($Co(NO_3)_2 \cdot 6H_2O$, 87.4 g) was dissolved in 200 milliliters of distilled water and heated to 90°C. The hot cobalt nitrate solution was poured into the stirring molybdenum solution forming a blue precipitate. The precipitate was filtered hot and the filter cake air dried for 1 hour with tamping. The filter cake was dried for 16 hours at 110° to 120°C then crushed to pass a 4-mesh sieve. The 4-mesh particles were calcined in a tube with flowing air for 6 hours at 590°C.

OXIDATION OF BUTANE

Example 8 — Oxidation of Butane with Sb/Ni/Mo Catalyst (1:0.24:0.14 atomic ratio)

A gaseous mixture of butane (0.8 mole percent) and air (99.2 mole percent) was passed over 29 g (19 mls) of an antimony-nickel-molybdenum catalyst (prepared as described in Example 1) contained in a ⅜ inch × 2½ foot stainless steel reactor. The contact time was 0.46 sec. at 402°C. The selectivity to maleic anhydride was 30% at 36% conversion of butane.

A unique feature of this catalyst is the constant selectivity with increase in conversion as shown by the data in Table 1.

TABLE I

CONTACT TIME-TEMPERATURE STUDY FOR THE OXIDATION OF BUTANE OVER AN Sb/Ni/Mo CATALYST

| Run No. | % C4 | Temp. °C | Time (T) (Sec) | % Conversion | % Selectivity | % Yield |
|---|---|---|---|---|---|---|
| 1 | 0.62 | 400 | 0.32 | 29 | 33 | 10 |
| 2 | 0.82 | 403 | 0.46 | 39 | 31 | 12 |
| 3 | 0.68 | 400 | 0.83 | 58 | 27 | 16 |
| 4 | 0.57 | 400 | 0.98 | 68 | 25 | 17 |
| 5 | 0.45 | 450 | 0.09 | 37 | 27 | 10 |
| 6 | 0.56 | 450 | 0.13 | 48 | 26 | 13 |
| 7 | 0.54 | 450 | 0.24 | 65 | 29 | 19 |
| 8 | 0.54 | 453 | 0.23 | 70 | 26 | 18 |
| 9 | | | | | | |

Example 9 — Oxidation of Butane with Antimony: Nickel: Molybdenum Catalyst

A gaseous mixture of butane (1.10 mole %) and air (98.90 mole %) was passed over 2.0 mls (2.44g) of an Sb/Ni/Mo catalyst prepared (as described in Example 2) contained in a 6 inches × ¼ inch stainless steel reactor. The contact time was 0.29 sec. at 450°C. The selectivity to maleic anhydride was 33 moles % at 27% conversion.

The effect of varying the ratio of Sb:Ni:Mo (i.e., Sb held constant (1.0) while Ni:Mo varied) is shown in Table IV.

TABLE II

| Run No. | (Sb = 1.0) Calc. | Anal. | Reaction Temp., °C | Time(T) (Sec) | % Conv. | % Sel. |
|---|---|---|---|---|---|---|
| 1 | 0.1:0.2 | 0.11:0.20 | 450 | 0.21 | 27 | 33 |
| | | | | 0.23 | 29 | 37 |
| 2 | 0.1:0.05 | 0.10:0.09 | 450 | 0.23 | 26 | 24 |
| 3 | 0.2:0.1 | 0.22:0.12 | 450 | 0.21 | 43 | 29 |
| 4 | 0.05:0.1 | 0.04:0.07 | 450 | 0.22 | 18 | 19 |

Example 10 — Oxidation of Butane with Antimony: Cobalt: Molybdenum Catalyst

A gaseous mixture of butane (0.60 mole %) and air (99.40 mole %) was passed over 23 mls (44.3 g) of an antimony: cobalt: molybdenum catalyst (prepared as described in Example (3) contained in a ⅜ inch × 2½ feet stainless steel reactor. The contact time was 0.81 sec. at 400°C. The selectivity to maleic anhydride was 34 mole % at 57% conversion.

Several additional runs were carried out with this catalyst to show that the selectivity was relatively constant up to at least 74% conversion. The data are shown in the following table:

TABLE III

OXIDATION OF BUTANE TO MALEIC ANHYDRIDE*

| Run No. | Temp. °C | % C4 | Time(T) (Sec) | % Conversion | % Selectivity |
|---|---|---|---|---|---|
| 1 | 403 | 0.67 | .38 | 37 | 35 |
| 2 | 402 | 0.59 | .80 | 55 | 33 |
| 3 | 402 | 0.65 | 1.52 | 74 | 28 |
| 4 | 401 | 1.17 | 2.42 | 90 | 18 |

*using 33 ml (39g) of antimony: cobalt: molybdenum

Example 11 — Oxidation of Butane with Antimony: Copper: Molybdenum Catalyst

A gaseous mixture of butane (0.84 mole %) and air (99.16 mole %) was passed over 16 mls. (12.49 grams) of an antimony:copper:molybdenum catalyst (prepared as described in Example 4) contained in a ⅜ inch × 2½ feet stainless steel reactor. The contact time was 0.66 sec. at 425°C. The selectivity to maleic anhydride was 40% at 36% conversion.

A second run using butane (0.70%) and air (99.3 mole %) resulted in 28% selectivity at 77% conversion. The contact time was 0.62 sec. at 502°C.

Example 13 — Oxidation of Butane with Antimony: Zinc: Molybdenum Catalyst

A gaseous mixture of butane (0.50 mole %) and air (99.50 mole %) was passed over 16 mls. (23.3 grams) of an Sb/Zn/Mo catalyst (prepared as described in Example 5) contained in a ⅜ inch × 2½ feet stainless steel reactor. The contact time was 1.04 sec. at 443°C. The selectivity to maleic anhydride was 34% at 24% conversion.

A second run using butane (1.16 mole %) and air (98.84 mole %) resulted in 28% selectivity at 41% conversion. The contact time was 2.08 Sec. at 443°C.

Example 13 — Comparative Runs with Cobalt and Nickel Molybdate Catalysts

The effect of the antimony oxide on the selectivity of the catalysts cobalt molybdate (as prepared in Example 6) and nickel molybdate (as prepared in Example 7) can be seen by comparing the data in Table I (above) with the data in Tables IV and V, below. The selectivity for the oxidation of butane to maleic anhydride over either the cobalt molybdate or the nickel molybdate catalyst decreases markedly above about 50–60% conversion. However, when antimony oxide is added to the catalyst, the selectivity does not decrease significantly until the conversion is above about 75%.

A. Cobalt-Molybdenum Catalyst

A gaseous mixture of butane (1.0 mole %) and air (99 mole %) was passed over 40.6 g (42 mls) of a cobalt-molybdenum-oxygen catalyst (prepared as described in Example 6) contained in a ⅜ inch × 2½ feet stainless steel reactor. The contact time was 0.94 seconds at 390°C. The selectivity was 28% at 29% conversion of butane. Similar runs under varying conditions are shown in Table IV below.

B. Nickel Molybdenum Catalyst

A gaseous mixture of butane (0.9 mole %) and air (99.1 mole %) was passed over 18.4 (30 mls) of a nickel-molybdenum-oxygen catalyst, (prepared as described in Example 7) contained in a ⅜ inch × 2½ feet stainless steel reactor. The contact time was 0.86 seconds at 506°C. The selectivity to maleic anhydride was 29% at 52% conversion of butane. Similar runs under varying conditions are shown in Table V below.

TABLE IV

PARAMETER STUDY OF THE OXIDATION OF BUTANE OVER A Co/Mo CATALYST[1]

| Run | % C4 | Temp. | Sec. | % Conv. | % Sel. | Yield |
|---|---|---|---|---|---|---|
| 1 | 1.05 | 390 | .93 | 30 | 31 | 9.3 |
| 2 | 1.01 | 390 | .93 | 45 | 26 | 11.7 |
| 3 | 1.02 | 390 | 1.96 | 64 | 17 | 10.9 |
| 4 | .94 | 422 | .38 | 47 | 28 | 13.2 |
| 5 | .98 | 422 | .66 | 60 | 28 | 16.8 |
| 6 | .98 | 422 | 1.34 | 79 | 15 | 11.7 |

[1]⅜" I.D. S.S. reactor, 18" bed.

TABLE V

PARAMATER STUDY OF THE OXIDATION OF BUTANE OVER A Ni/Mo CATALYST

| Run | % C4 | Temp. | Sec. | % Conv. | % Sel. | Yield |
|---|---|---|---|---|---|---|
| 1 | 0.85 | 500 | 0.46 | 36 | 27 | 10 |
| 2 | 0.91 | 506 | 0.86 | 52 | 29 | 15 |
| 3 | 0.96 | 500 | 1.51 | 70 | 21 | 15 |
| 4 | 0.81 | 499 | 2.10 | 81 | 17 | 14 |

Example 14 — Effect of Calcination Temperatures

The following table demonstrates the effect of calcination temperatures on the color and selectivity of certain of catalysts of this invention.

It can be seen from this Table (Table VI) that when the calcination temperature is held at 600°C for up to 16 hours, the catalyst possesses activity but there is no selectivity to maleic anhydride. At a temperature of 710°C, the calcination time must be held beyond 8 hours before any selectivity is seen. When the calcination temperature is increased to 800° for 3–4 hours, the selectivity increases to 25–33%. However, if the temperature is held at 800° for 8 hours, there is some decrease in the selectivity.

TABLE VI

EFFECT OF CALCINATION TIME AND TEMPERATURE ON THE ACTIVITY AND SELECTIVITY OF AN Sb/Ni/Mo CATALYST FOR THE OXIDATION OF BUTANE TO MALEIC ANHYDRIDE

| Run No. | Calc. Temp. °C | Calc. Time (hrs.) | Reaction Temperature °C | τ | Conversion | Selectivity | Comments |
|---|---|---|---|---|---|---|---|
| 1 | 25–600 | 7 | 500 | 0.47 | 19 | 0 | Light Yellow |
| 2 | 600 | 8 | 500 | 0.47 | 30 | 0 | Light Yellow |
| 3 | 600 | 16 | 470 | 1.40 | 44 | 0 | Light Yellow |
| 4 | 600 | 16 | 500 | 0.24 | 14 | 0 | Light Yellow |
| 5 | 25–710 | 8 | 450 | 0.30 | 8 | 0 | Light Yellow |
| 6 | 710 | 8 | 490 | 0.32 | 13 | 0 | Yellow-green |
| 7 | 710 | 16 | 450 | 0.31 | 18 | 11 | Light Green |
| 8 | 800 | 3 | 450 | 0.25 | 32 | 30 | Light Green |
| 9 | 800 | 4 | 450 | 0.28 | 30 | 27 | Light Green |
| 10 | 800 | 4 | 450 | 0.28 | 26 | 33 | Light Green |
| 11 | 800 | 4 | 450 | 0.28 | 28 | 25 | Light Green |
| 12 | 800 | 8 | 450 | 0.48 | 19 | 19 | Light Green |

INCREASED $C_4^=$: $O_2$ RATIO

In a further embodiment of the invention it has been found that when the concentration of butane, relative to the amount of oxygen, is increased in the feed stream, the selectivity for maleic anhydride is likewise increased significantly. Customarily, as in the above-described process, the concentration of hydrocarbon in the feed stream is kept low for safety purposes, i.e., at mol ratios of about 1:4 or lower of hydrocarbon to oxygen, and preferably ratios of 1:10 or lower, e.g., 1:20. Under these conditions, it has been found that the selectivity for maleic anhydride is generally between 25 and 50%.

It has now been found that, contrary to general practice and expectations, when the oxygen is employed as pure oxygen rather than diluted with inert gases, e.g., with nitrogen as in air, and the concentration of butane relative to the oxygen is increased to ratios of greater than 1:4, preferably greater than 1:1, in order to operate outside the explosive limits, the selectivity for maleic anhydride is increased about 20% over what is obtained with a hydrocarbon— lean feed but without any dangerous side effects. Thus, it has been found that ratios of greater than 1:4 may be employed, and preferably ratios in the range of about 1:1 to 20:1 of hydrocarbon to oxygen. Furthermore, a significant increase in space-time-yield is obtained as shown in the following table wherein the space-time-yield increased from 30 to 103 when the $C_4:O_2$ ratio was changed from 1:20 to 1.6:1 and pure oxygen was employed in place of air.

This feature is of great economic significance when designing a commercial plant. There is an obvious advantage with the higher STY in that the reactor size can be reduced, e.g., in the above case the size could be reduced by a factor of 3.

The following example, which forms part of the subject matter disclosed and claimed in a related application, now U.S. Pat. No. 3,899,516 in the name of Alan F. Dickason, illustrates this improved embodiment of the invention.

Example 15

In accordance with the procedures of Example 8, a gaseous mixture of butane (65 mole percent) and oxygen (35 mole percent) was passed over 2 g of antimony-nickel-molybdenum catalyst (prepared as described in Example 1). The conditions and results obtained are summarized in the following table. For sake of comparison a second run using the conditions described in Table I above (Run 4) are also set forth in this table.

TABLE VII

| Catalyst | $C_4:O_2$ | Time (Sec) | Temp. (°C) | % Conv. | % Sel. | Space Time Yield |
|---|---|---|---|---|---|---|
| Sb/Ni/Mo | 1.6:1 | 0.20 | 428 | 2.4 | 51 | 103 |
| Sb/Ni/Mo | 1:20 | 0.98 | 400 | 68 | 25 | 30 |

The invention claimed is:

1. A process for preparing a catalyst composition useful for the vapor phase oxidation of butane to maleic anhydride which comprises dissolving an antimony salt in water, adjusting the pH of the solution to about 6.5 to precipitate said salt, adding to said precipitate an aqueous solution of a mixture of a molybdenum salt and a salt of nickel, cobalt, copper or zinc, drying the resulting composition at about 110° to 130°C and crushing it to small particle size, and thereafter calcining the particles at a temperature of from about 750° to 850°C for at least about 2 hours.

2. The process according to claim 1 wherein the final catalyst composition contains from about 40 to 90 atomic percent antimony, from about 1 to 20 atomic percent molybdenum, and from about 5 to 40 atomic percent of nickel, cobalt, copper or zinc, said atomic percent being based on the total metals of the composition.

* * * * *